United States Patent
Banks

(10) Patent No.: US 6,556,027 B2
(45) Date of Patent: Apr. 29, 2003

(54) LOW COST, ON-LINE CORROSION MONITOR AND SMART CORROSION PROBE

(75) Inventor: Rodney H. Banks, Aurora, IL (US)

(73) Assignee: Ondeo Nalco Company, Naperville, IL (US)

(*) Notice: Subject to any disclaimer, the term of this patent is extended or adjusted under 35 U.S.C. 154(b) by 0 days.

(21) Appl. No.: 09/758,928

(22) Filed: Jan. 12, 2001

(65) Prior Publication Data

US 2002/0105346 A1 Aug. 8, 2002

(51) Int. Cl.[7] .............................. G01R 27/08
(52) U.S. Cl. .............................. 324/700; 324/690
(58) Field of Search ......................... 324/690, 691, 324/696, 700

(56) References Cited

U.S. PATENT DOCUMENTS

| | | | | |
|---|---|---|---|---|
| 4,040,931 A | * | 8/1977 | Wilson | 204/404 |
| 4,238,298 A | | 12/1980 | Tsuru et al. | 205/775.4 |
| 4,831,324 A | | 5/1989 | Asakura et al. | 324/615 |
| 4,863,572 A | * | 9/1989 | Jasinski | 205/775.5 |
| 5,446,369 A | * | 8/1995 | Byrne et al. | 324/700 |
| 5,448,178 A | | 9/1995 | Chen et al. | 205/775.5 |
| 5,854,557 A | * | 12/1998 | Tieffnig | 324/700 |
| 5,896,034 A | * | 4/1999 | Marshall | 324/700 |
| 6,320,395 B1 | * | 11/2001 | Bosch et al. | 324/700 |
| 6,348,803 B1 | * | 2/2002 | Mohr | 324/642 |
| 6,428,684 B1 | * | 8/2002 | Warburton | 205/775 |

* cited by examiner

Primary Examiner—Christine Oda
Assistant Examiner—Walter Benson
(74) Attorney, Agent, or Firm—Kelly L. Cummings; Margaret M. Brumm; Thomas M. Breininger

(57) ABSTRACT

Devices, methods and systems are provided for monitoring of industrial processes. Devices and systems are provided which include a controller module connected to a probe module having a specified metallurgy and a resistor module having a specified resistance value which is capable of identifying the metallurgy of the probe module to the controller module. A resistor device including a resistor having a resistance value which identifies a type of metallurgical material is also provided. The devices and systems provided are inexpensive, portable, easy to set-up and operate by unskilled personnel, may be connected to both desktop and portable computerized devices and can provide real-time monitoring of industrial processes.

12 Claims, 1 Drawing Sheet

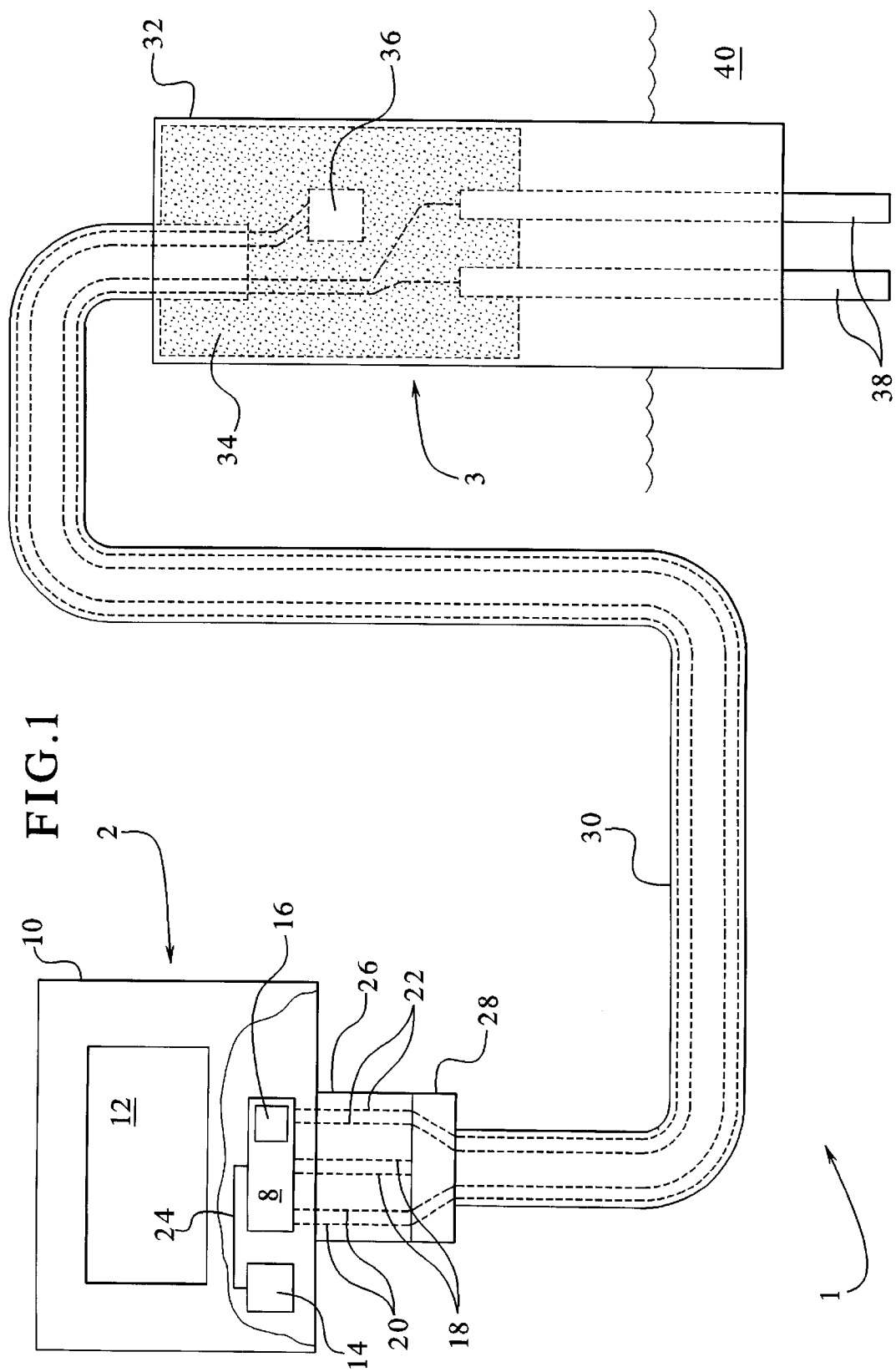

LOW COST, ON-LINE CORROSION MONITOR AND SMART CORROSION PROBE

BACKGROUND OF THE INVENTION

The present invention generally relates to a device, method and system for industrial processing. More specifically, the present invention relates to a device, method and system for monitoring corrosive industrial processes.

It is, of course, generally known that various industrial processes produce corrosive by-products. Such corrosive by-products frequently corrode industrial equipment, increase production costs, and create production delays. Thus, corrosion monitoring is a valuable tool which can alleviate such process upsets.

At present, typically on-line corrosion monitoring equipment for industrial processing is relatively expensive and cumbersome to use. Such corrosion monitoring devices frequently contain large and complicated monitoring components which are not portable and must be placed in a permanent fixed position in relation to the industrial process being monitored. Moreover, because such equipment is large, complicated and cumbersome, it may be difficult to set up and operate in an efficient manner by either skilled or unskilled personnel.

It is generally known that currently available corrosion monitoring devices are capable of storing data for later downloading to other computerized devices. However, such corrosion devices often lack the ability to provide real-time corrosion monitoring or the capability to communicate with more portable computerized devices such as laptop or hand-held computers.

Another problem sometimes encountered with currently available corrosion monitoring devices is that such devices are not disposable. Although some corrosion monitoring devices offer replaceable components, many function improperly and are often very expensive.

The disposability problem can be further exacerbated because many currently available monitoring devices do not offer waterproof or weatherproof enclosures. Thus, moisture and exposure to other environmental elements harms many of the internal components of such devices. Thus, the life span, functional consistency and monitoring reliability of at least some currently available corrosion monitoring devices can be significantly reduced. Such detrimental environmental effects can also significantly increase the operation and maintenance costs of those devices as well.

A still further problem encountered with at least some prior art corrosion monitoring devices is the substantial number of inaccurate readings. In most instances, the inaccuracy occurs because the monitoring device is incapable of identifying the type of metallurgical material utilized by the device to determine corrosion rate.

For example, within most corrosion monitoring devices, an electrode probe having a specific metallurgy is used to determine corrosion rate of an industrial process. The corrosion rate is determined based upon the corrosivity of the industrial process upon the specific type of metallic probe electrode used. If the metallurgy of the probe changes or cannot be determined by the monitoring device, frequent and substantial inaccurate readings result which must later be accounted for and corrected. To correct such misreadings, additional operating costs are incurred.

Improved device, method and system for monitoring industrial processes would therefore be desirable.

SUMMARY OF THE INVENTION

The present invention relates to an improved device, method and system for monitoring an industrial process. More specifically, the present invention relates to an improved device, method and system for monitoring industrial corrosive cooling water treatment processes.

To this end, the present invention provides a device comprising a controller module; a probe module which operably communicates with the controller module; and a resistor module which operably communicates with the controller module, wherein the resistor module is capable of identifying the probe module to the controller module.

The present invention also provides a corrosion monitoring system comprising a controller module; a probe module having at least one metallurgical probe electrode which operably communicates with the controller module; and a resistor module having a resistance value which operably communicates with the controller module, wherein the resistance value identifies the metallurgy of the probe electrode to the controller module.

Additionally, the present invention also provides a method of determining corrosion rate comprising the steps of providing a corrosion monitoring device comprising a controller module; a probe module which operably communicates with the controller module; and a resistor module which operably communicates with the controller module; placing the probe module within a solution; charging the probe module and resistor module with a current via the controller module; identifying the type of probe module by the controller module based upon the resistance value of the charged resistor module; and determining the rate of corrosion by the controller module after the probe module has been identified.

Moreover, the present invention further provides a probe device comprising an electrode and a resistor having a resistance value which identifies the electrode.

Additional features and advantages of the present invention are described in and will be apparent from, the detailed description of the presently preferred embodiments and from the drawings.

BRIEF DESCRIPTION OF THE FIGURES

FIG. 1 illustrates a perspective view of an embodiment of the device of the present invention.

DETAILED DESCRIPTION OF THE PRESENTLY PREFERRED EMBODIMENTS

The present invention relates to devices, methods and systems for monitoring corrosive industrial processes. More specifically, the present invention relates to devices, methods and systems for monitoring corrosion of industrial cooling water treatment systems.

Referring now to the drawings wherein like numerals refer to like parts, FIG. 1 illustrates an embodiment of the monitoring device 1 of the present invention from a perspective view. In the illustrated embodiment, monitoring device 1 includes two main components. Those main components, as can be seen in FIG. 1, include controller module 2 and probe module 3 which operably communicate with one another via cable 30.

Focusing upon controller module 2 specifically, the module further comprises a controller body 10, which includes a circuit board 8, a display device 12 and a power source 14. Circuit board 8 further operably communicates with microcontroller 16. Circuit board 8 is supplied with power from power source 14 via electrical cable 24 and circuit board 8 redirects that power to microcontroller 16 and conductor pairs 20, 22.

Moreover, as industrial processes are monitored by monitoring device 1 of the present invention, data is collected and stored by microcontroller 16 for later downloading to other computerized devices. To download such information from microcontroller 16 to those other computerized devices, a data cable 18 extending from circuit board 8 is utilized.

Additionally, as current is supplied to circuit board 8 and redirected to conductor pairs 20, 22 which are connected to and extend from circuit board 8. That current is then provided to probe module 3 and its internal components via cable 30 which provides operable communication between controller module 2 and probe module 3 by housing conductor pairs 20, 22 as can be seen in FIG. 1.

Controller body 10 of monitoring device 1 may be manufactured from any material, preferably a plastic material capable of withstanding industrial compounds such as corrosive substances and environmental forces. In a preferred embodiment of the present invention, controller body 10 is made from a plastic material which is capable of withstanding corrosion as well as indoor and outdoor environmental elements.

An advantage of the present invention is that monitoring device 1 is preferably manufactured from materials which can withstand the harsh elements found within industrial processes and those of the environment. In doing so, the present invention can provide industrial process monitoring without disruption or inaccurate readings due to those forces.

Thus, it should be appreciated by those skilled in the art that power source 14 provides current to multiple components within monitoring device 1 which may be utilized in a variety of manners and levels as needed to operate the device according to the principles of the present invention.

In a preferred embodiment of the present invention, power source 14 is a battery. Thus, monitoring device 1 does not have to be permanently positioned in one location near an electrical outlet. By being battery powered, monitoring device 1 has the advantage of becoming more compact, portable and safe from electrical shock hazards unlike conventional monitoring devices which must be connected to an alternating current electrical outlet in order to operate properly.

Battery types which are suitable for use as power source 14 include, but are not limited to, alkaline batteries; lithium batteries; zinc-air batteries; rechargeable nickel-cadmium batteries; and rechargeable nickel-metal hydride batteries. Alkaline batteries are most preferred due to their widespread commercial availability and low cost.

Microcontroller 16 of the present invention may be any conventional microcontroller found within the software arts. Preferably, microcontroller 16 is a mixed signal microcontroller such as a 68-pin, 16-bit RISC microchip having a fast execution time and lower power consumption through the use of a 32.768-kilohertz watch crystal. Moreover, it is also preferable that microcontroller 16 includes an LCD display driver, an A/D converter, timers, and an array of digital I/O pins to achieve the monitoring, displaying, and data communication principles of the present invention.

Microcontroller 16 of the present invention is also capable of storing collected data utilizing memory storage devices generally associated with microcontrollers such as non-volatile memory (EEPROM) and random access memory (RAM). Additionally, microcontroller 16 can provide that stored data to other computerized and Internet based devices by downloading such information using data cable 18.

Data cable 18 is capable of providing operable communication between controller module 2 and conventional desktop and portable computerized devices. It should be appreciated by those skilled in the art that data cable 18 can be any readily available communication port including, but not limited to, a parallel connection, a serial connection, an optical connection, a fire wire connection, an analog pin connection, derivatives thereof and combinations thereof.

An advantage of the present invention is that monitoring device 1 can be connected to a variety of computerized and Internet-based devices. Thus, monitoring device 1 of the present invention via data cable 18 may be connected to desktop computerized devices, portable devices such as laptop and palmtop computers and Internet-based devices such as LAN networks.

In doing so, monitoring device 1 of the present invention can provide industrial consumers up-to-date information immediately if the device is connected to a running computer or to the Internet. Such on-line capabilities allows for closer monitoring of industrial processes, especially those which are sensitive and must be constantly monitored. The present invention can provide real-time monitoring of industrial processes in an on-line manner unlike many conventional monitoring devices.

Moreover, by allowing monitoring device 1 the capability to interact with portable and desktop computerized devices, the present invention creates a variety of ways in which stored information can be downloaded easily by the industrial consumer. Thus, the monitoring device of the present invention can be utilized in an industry wide fashion because the device can operably communicate with most, if not all, conventional computerized systems and networks.

To display information, microcontroller 16 in conjunction with circuit board 8 operably communicates with display device 12. Preferably, display device 12 is a liquid crystal display, which is capable of displaying a variety of numbers, texts and symbols. For example, in a preferred embodiment of the present invention, display device 12 is capable displays numbers in the range of 0.00–99 including the decimal points as well as textual letters such as the letter "E" to indicate and display an error code.

An additional advantage of the present invention is provided through the real-time display of information via display device 12. Rather than merely downloading stored information from microcontroller 16 via circuit board 8 and data cable 18, users of monitoring device 1 can utilize display device 12 to receive information at a specific moment in time.

To connect controller module 2 via cable 30 to probe module 3, a cable connection port 26 is provided within monitoring device 1. (FIG. 1.) Cable connection port 26 provides a connection point for cable connector 28 such that cable 30 provides operable communication via conductor pairs 20, 22 for controller module 2 to probe module 3 and various internal components therein. Thus, it should be appreciated by those skilled in the art that cable connection port 26 provides dual functionality for monitoring device 1 of the present invention. In doing so, cable connection port 26 reduces the number of connection points required for monitoring device 1 which enhances its lower cost, portability and compact size.

Cable 30 can be made of any material which is capable of housing electrical wires and cables like those of conductor pairs 20, 22. Preferably, cable 30 is an insulative material coated with an additional material such as plastic which is capable of withstanding industrial and environmental forces.

Referring now to probe module 3, the probe module includes a probe module body 32 which further includes an epoxy 34. Embedded within epoxy 34 are cable 30 including conductor pairs 20, 22; resistor module 36; and one end of a pair of probe electrodes 38. (FIG. 1.)

As can be seen in FIG. 1, conductor pair 20 extends from cable 30 within probe body 32 and epoxy 34 to probe electrodes 38. In doing so, current provided from power source 14 to circuit board 8 and is redirected from circuit board 8 via conductor pair 20 to probe electrodes 38. In contrast, conductor pair 22 extends from cable 30 within probe body 32 and epoxy 34 to resistor module 36 and that conductor pair 22 is provided power from circuit board 8 which was originally provided to circuit board 8 from power source 14.

Cable 30 including conductor pairs 20, 22; resistor module 36; and probe electrodes 38 are embedded within epoxy 34 to prevent their exposure to indoor and outdoor elements, especially moisture. By embedding these internal components of probe module 3 within epoxy 34, the module can provide accurate measurements of industrial processes to a greater extent than could be previously achieved with other conventional monitoring devices because disruptive environmental forces are reduced or eliminated.

For example, by embedding probe electrodes 38 within epoxy 34 as shown within FIG. 1, the probe electrodes are spaced apart from one another and prevented from contacting aqueous substances at their connection point to conductor pair 22. This in turn reduces or prevents probe electrodes 38 from shorting out. By eliminating such shorting out of probe electrodes 38, inaccurate voltage readings from the electrodes by microcontroller 16 are significantly reduced or eliminated.

Moreover, by embedding probe electrodes 38 within epoxy 34, local corrosion phenomena such as crevice and pitting corrosion are also substantially reduced or eliminated. Such corrosive prevention enhances the functional life span of monitoring device 1 as well as that of probe electrodes 38.

Probe module 3 can be manufactured from any suitable materials which are capable of withstanding environmental as well as industrial forces. In a preferred embodiment of probe module 3, probe body 32 is made from Garolite. Garolite is a fiber-epoxy laminate which is very strong and chemically resistant to corrosive substances, does not absorb water and bonds strongly to epoxy potting materials. However, it should be appreciated by those skilled in the art that probe body 32 may be manufactured from any material which is chemically resistant to water, but forms a chemical bond to epoxy such as polyvinyl chloride.

To enhance the weatherproofing capabilities of probe module 3, probe body 32 further includes epoxy 34. Any conventional epoxy material may be utilized which is suitable for use within industrial processes and which can withstand environmental pressures. Use of epoxy 34 within probe module 3 provides a water and weather-tight seal around conductor pairs 20, 22; cable 30; resistor module 36; and to one end of probe electrodes 38 in relation to probe body 32.

By forming such a seal, protection of those components is enhanced. Such protection decreases replacement costs of the present invention because its life span is significantly increased.

Resistor module 36 within FIG. 1 may be any currently available resistor. Preferably, resistor module 36 is small, stable and inexpensive such that its impedance to a current is easy to measure. In a preferred embodiment of the present invention, resistor module 36 is a metal film resistor having a 1% tolerance and 100 ppm/degree Celsius coefficient.

Under control by microcontroller 16, current from power source 14 is sent by connector pair 22 to resistor module 36. Resistance to that current by resistor module 36 is measured and monitored by microcontroller 16.

In doing so, the monitoring device of the present invention provides an identification function unlike conventional monitoring devices. When current is passed through resistor module 36, microcontroller 16 calculates a resistance value. Based upon that resistance value, microcontroller 16 is then capable of identifying the type of probe module 3 to controller module 2.

More specifically, microcontroller 16 is capable of identifying the type of probe electrode 38 of probe module 3. Such identification can be done because monitoring device 1 utilizes a specific resistor module 36 to identify a type of material from which probe electrodes 38 are constructed.

For example, if probe electrode 38 has a specific type of metallurgy such as copper, then resistor module 36 having an impedance ohm value of 1100 is specifically used within one embodiment of monitoring device 1 to identify only copper probe electrodes. In doing so, each time microcontroller 16 determines a resistance value of 1100 ohms from resistor module 36, the microcontroller is capable of identifying probe electrodes 38 as being copper electrodes.

Unlike conventional monitoring devices utilizing probe electrodes, the present invention provides a method of identifying a variety of electrodes used for different forms of industrial processing. In essence, probe electrode 38 acts as a "smart" probe because it can identify itself to microcontroller 16 of controller module 2 using resistor module 36 of probe module 3.

As controller module 2 is used with different embodiments of probe module 3 and different forms of probe electrodes 38, controller module 2 can quickly and efficiently identify the type of probe module it is connected to for use within a variety of industrial processes. Moreover, because controller module 2 is able to identify probe electrodes 38 of probe module 3, controller module 2 can provide more accurate monitoring of industrial processes.

For example, monitoring device 1 can be used to monitor corrosive industrial processes each of which reacts differently to each type of metallurgical probe electrode 38 placed within probe module 3. By identifying the type of metallurgy probe electrode 38 via resistor module 36, controller module 2 can adjust corrosive measurements accordingly once the metallurgical nature of probe electrode 38 has been deduced.

Conventional monitoring devices are less accurate than the monitoring device 1 of the present invention because such devices do not provide probe identification. Thus, the present invention significantly increases the accuracy to which an industrial process can be monitored than could be done previously.

Probe electrodes 38 of the present invention can be of any conventional monitoring material utilized to monitor industrial processes. Preferably, probe electrodes 38 are made of a metallurgical material including, but not limited to, copper, nickel, copper and nickel alloys, steel, admiralty brass, derivatives thereof and combinations thereof.

Furthermore, it should also be appreciated by those skilled in the art that probe module 3 and resistor module 36, each can be used separately with conventional monitoring devices to upgrade and simplify those devices in monitoring industrial processes.

In a further embodiment of the present invention, a probe device is provided. The device comprises an electrode and a resistor having a resistance value which identifies the electrode. The electrode of the probe device is a material chosen from the group consisting of copper, nickel, nickel and copper alloys, steel, admiralty brass, derivatives thereof and combinations thereof. Preferably, the probe device is portable and battery powered.

It should be appreciated by those skilled in the art that the monitoring device of the present invention can have numerous alternative embodiments once the principles of the present invention have been grasped.

The monitoring device 1 of the present invention offers numerous benefits over prior art monitoring devices. Monitoring device 1 is comprised of components which are not of large size such that controller module 2 and probe module 3 of monitoring device 1 are portable. Additionally, all of the components of the present invention are small adding to the compact nature of monitoring device 1.

Additionally, because of the reduced size of components and use of battery power, monitoring device 1 of the present invention is inexpensive to manufacture. Thus, the present invention offers a portable, yet highly accurate, monitoring device which costs significantly less than currently available monitoring devices.

Moreover, it should be appreciated by those skilled in the art that monitoring device 1 of the present invention is designed for easy set-up and use. The device has been constructed in such a manner that it can be simply installed operated by unskilled personnel in an electrically safe manner.

To install monitoring device 1, an unskilled worker must merely place controller module 2 in an appropriate location where it can be mounted near flowing sample 40 and connect probe module 3 to controller module 2 via connector 28 of cable 30 to connector 26 of controller module 2 and put probe module 3 into contact with flowing sample 40 such that electrodes 38 are completely immersed in flowing sample 40. Since monitoring device 1 is preferably battery powered once the batteries have been installed, the device is always on.

The entire installation of the device is simple and a worker does not have to provide any further programming, pressing of buttons, operation of instructional menus, calibrations, or auxiliary power source hook up to operate monitoring device 1 of the present invention. In addition, since monitoring device 1 is battery powered, the unskilled worker doesn't have to constantly turn the device on or off, which further enhances its simplicity of operation and installation.

Because of its ease of installation and operation, the present invention substantially simplifies the manner in which an industrial process is monitored by personnel. Such simplicity provides an advantage over currently available monitoring devices which are more complicated and cumbersome to install and operate.

In operation, monitoring device 1 of the present invention can be used to monitor a variety of industrial processes. Monitoring device 1 can be used to monitor such processes including, but not limited to, corrosion; electrical conductivity; temperature; localized corrosion phenomena; pitting tendency, derivatives thereof and combinations thereof. Preferably, monitoring device 1 of the present invention is used to monitor corrosion which occurs during industrial processing. More preferably, monitoring device 1 of the present invention is utilized to monitor corrosion of cooling water industrial treatment systems.

In another embodiment of the present invention, a method of determining corrosion rate is provided. The method comprises the steps of providing a corrosion monitoring device such as monitoring device 1 which comprises a controller module 2; a probe module 3 which operably communicates with the controller module; and a resistor module 36 which is capable of identifying the probe module to the controller module.

The probe module 3 is placed within a sample solution 40 such that probe electrodes 38 are fully immersed with the solution. Then, in probe module 3, resistor module 36 is charged with a current via controller module 2. The identity of probe module 3 is then determined by controller module 2 based upon the resistance value of the charged resistor module. Finally, the rate of corrosion based upon formulas known within the art is determined by controller module 2 after probe module 3 has been identified.

In a preferred embodiment of the method, device 1 of the present invention produces a current via power supply 14 which is conducted via electrical cable 24 to circuit board 8 and redirected to microcontroller 16 and conductor pairs 20, 22. In doing so, current is carried to electrode probe 38 via conductor pair 20, to create a series circuit through sample solution 40.

Microcontroller 16 is capable of determining the metallurgy of probe electrodes 38 based upon the resistance value or impedance of resistance module 36. Once probe electrodes 38 have been identified, the corrosion rate of the electrodes in sample solution 40 is determined using a well known linear polarization resistance formula.

Linear polarization resistance of a corroding metal is the slope of potential versus current density at the corrosion potential of the electrode and is inversely proportional to the corrosion current or corrosion rate. Using a simple factor, corrosion rate can be calculated from a measured value of the linear polarization resistance.

Additionally, solution resistance i.e., the electrical resistance of sample 40 between the electrodes 38, must be accounted for as well. Most often, it is a significant portion of the total resistance measured and must be subtracted out to get an accurate value of the linear polarization resistance relative to corrosion rate. Solution resistance is independent of metallurgy and varies with sample composition and temperature.

More quantitatively, the equivalent circuit for an electrode in an aqueous sample is a resistor and a capacitor connected in parallel. The resistance is the polarization resistance, $R_p$, and the capacitor, $C_p$, comes about due to the nature of the metal-fluid interface called the double layer.

For example, the pair of probe electrodes 38 can be represented by two $R_pC_p$ elements coupled in series to the solution resistance, $R_s$, of sample solution 40. Therefore, the total dc resistance $R_{tot}$, can be expressed as the equation $R_{tot}=R_s+2R_p$.

Two resistances then are directly determined by monitoring device 1 of the present invention. Those resistances are $R_{tot}$ and $R_s$, from which $R_p$ is obtained by their difference. Corrosion rate is calculated from the equation of mpy=$k/R_p$, where mpy is in mils per year and k as is known in the Art as a proportionality constant that is unique to the metallurgy of probe electrodes 38.

In order to find $R_{tot}$ and $R_s$, the two probe electrodes 38 are inserted in the feedback loop of an op amp in the inverting configuration. One of probe electrodes 38 is maintained at power supply 14's ground potential while the other probe electrode 38 is driven by the output of the op amp such that the current forced through that probe electrode is equal in magnitude to that deliberately injected into the input node of the op amp. Knowing the input current, i, and output voltage, v, resistance is calculated as R=v/i.

Therefore, to determine corrosion rate, a dc current, $i_{dc}$, is injected into probe electrodes 38 to determine $R_{tot}$, the total resistance. As both probe electrodes 38 $C_p$s charge up, the output voltage approaches the value $R_{tot} \times i_{dc}$. Preferably, in order to prevent polarizing probe electrodes 38, the voltage change is kept within 25 mV and steps of both polarities are used.

An estimate of $R_{tot}$, is then made by sending a small test current to probe electrodes 38. The resultant voltage change and impedance is monitored by microcontroller 16. With that result, an appropriate current is computed for a 25 mV change.

Then, zero current is injected into probe electrodes 38 giving a voltage of $V_0$, followed by a current $i_{dc}$ that will cause a change of approximately +25 mV ($V_1$). A current that will give a change of −25 mV ($V_2$) is then injected followed by another zero current step giving a voltage of $V_3$. In doing such a sequence of currents, $R_{tot}$ can then be calculated from the four readings using the equation $R_{tot} = (2V_1 - V_0 + V_3 - 2V_2)/4i_{dc}$.

A similar procedure is used to determine $R_s$ by imposing a 1.3 kHz square wave of sufficient current amplitude ($i_{pk}$) to cause a +/−40 mV change. In doing so, the double layer capacitance imposes negligible impedance effectively shorting out both probe electrodes 38. Thus, peak-to-peak amplitude voltage change becomes $R_s \times i_{pk}$. $R_s = V/i_{pk}$. Once $R_s$ has been determined, it is subtracted from $R_{tot}$ and $R_p$ and thus corrosion rate is calculated. $R_p$ is then found as $R_p = \frac{1}{2}(R_{tot} - R_s)$ and corrosion rate=$k/R_p$.

It should be appreciated by those skilled in the art that the corrosion measurement function of the monitoring device 1 of the present invention consists of many operations. For example, monitoring device 1 initially takes a battery reading of power source 14, turns on analog power via microcontroller 16, connects the probe electrodes to the circuitry and performs the corrosion measurements as referred to above.

Therefore, the method of the present invention provides a simplified manner of determining corrosion rate for unskilled personnel because the method calculates corrosion rate for those personnel without additional calibrations, programming, and monitoring steps being performed. All such steps are completed with the unitary monitoring device used within the method.

In a still further embodiment of the present invention, a corrosion monitoring system is provided. The corrosion monitoring system comprises a controller module 2; a probe module 3 having at least one metallurgical probe electrode 38 which operably communicates with the controller module 2; and a resistor module having a resistance value which operably communicates with the controller module 2, wherein the resistance value identifies the type of metallurgy of the probe electrode 38 to the controller module 2 as can be seen in FIG. 1.

The system may further include a display device 12 which operably communicates with the controller module 2. Further, the controller module 2 of the system is capable of determining corrosion rate and storing corrosion rate data.

The system is also capable of operably communicating with desktop and portable computerized devices via the controller module 2. Preferably, the system is battery powered and portable.

The system of the present invention provides industrial process consumers a single device which is inexpensive, easy to install and operate, portable and connectivity with a variety of computerized devices to provide real-time as well as stored data capabilities. Moreover, because the system like monitoring device 1 of the present invention is made from inexpensive materials and is compact, the entire system once utilized can be disposed of in without substantial cost. Conventional monitoring devices and systems cannot provide such disposability.

Therefore, the devices, methods and systems of the present invention provide a simplified manner of determining corrosion rate which is more accurate than currently available monitoring devices. Moreover, the devices, methods and systems of the present invention do so in a compact, portable, battery powered, on-line, disposable and inexpensive manner which could not be achieved previously with prior art devices.

It should be understood that various changes and modifications of the presently preferred embodiments described herein will be apparent to those skilled in the art. Such changes and modifications can be made without departing from the spirit and scope of the present invention without diminishing its intended advantages. It is, therefore, intended that such changes and modifications be covered by the appended claims.

What is claimed is:

1. A corrosion monitoring device comprising:
   a controller module;
   a probe module which operably communicates with the controller module;
   a resistor module which operably communicates with the controller module;
   wherein the probe module includes at least two metallurgical probe electrodes;
   wherein the resistor module is capable of identifying the type of probe module to the controller module because said resistor module includes a resistance value which identifies the type of metallurgy of the probe electrodes to the controller module;
   wherein said corrosion monitoring device further includes a display device which operably communicates with the controller module;
   wherein said corrosion monitoring device can be operated without having to have the operator provide any further programming, pressing of buttons, operation of instructional menus, calibrations or auxiliary power source hook up.

2. The device of claim 1, wherein the device is portable.

3. The device of claim 1, wherein the device is battery powered.

4. The device of claim 1, wherein the controller module further includes a microcontroller capable of determining corrosion rate.

5. The device of claim 4, wherein said microcontroller is further capable of providing and storing corrosion rate data.

6. The device of claim 5, wherein the controller module is capable of operably communicating with desktop and portable computerized devices.

7. A corrosion monitoring system comprising:
   a controller module;
   a probe module having at least two metallurgical probe electrodes which operably communicate with the controller module;

a resistor module having a resistance value which operably communicates with the controller module, wherein the resistance value identifies to the controller module the type of metallurgy of the probe electrodes;

wherein said corrosion monitoring system further includes a display device which operably communicates with the controller module;

wherein said corrosion monitoring system can be operated without having to have the operator provide any further programming, pressing of buttons, operation of instructional menus, calibrations or auxiliary power source hook up.

8. The corrosion monitoring system of claim 7, wherein the controller module is capable of determining corrosion rate and storing corrosion rate data.

9. The corrosion monitoring system of claim 7, wherein the controller module is capable of operably communicating with desktop and portable computerized devices.

10. The corrosion monitoring system of claim 7, wherein the system is portable.

11. The corrosion monitoring system of claim 10, wherein the system is battery powered.

12. A method of determining corrosion rate comprising the steps of:

(a) providing a corrosion monitoring device; wherein said corrosion monitoring device comprises:
  (i) a controller module;
  (ii) a probe module having at least two metallurgical probe electrodes which operably communicate with the controller module;
  (iii) a resistor module having a resistance value which operably communicates with the controller module, wherein the resistance value identifies to the controller module the type of metallurgy of the probe electrodes;

(b) placing the probe module within a solution;

(c) charging the resistor module with a current via the controller module;

(d) identifying the type of probe module by the controller module based upon the resistance value of the charged resistor module; and (iv) determining the rate of corrosion by the controller module after the probe module has been identified;

wherein said corrosion monitoring device further includes a display device which operably communicates with the controller module.

* * * * *